US008709013B2

(12) United States Patent
Lombardo

(10) Patent No.: US 8,709,013 B2
(45) Date of Patent: Apr. 29, 2014

(54) CANNULATED DRILL BIT WITH RADIALLY OFFSET CUTTING EDGE

(75) Inventor: Giuseppe Lombardo, New Port Richey, FL (US)

(73) Assignee: Linvatec Corporation

( * ) Notice: Subject to any disclaimer, the term of this patent is extended or adjusted under 35 U.S.C. 154(b) by 1551 days.

(21) Appl. No.: 11/826,873

(22) Filed: Jul. 19, 2007

(65) Prior Publication Data

US 2009/0024130 A1   Jan. 22, 2009

(51) Int. Cl.
  *A61B 17/16* (2006.01)
(52) U.S. Cl.
  USPC ............................................ 606/80; 606/180
(58) Field of Classification Search
  USPC ................... 408/199–233; 606/79–80, 86 R, 606/167–168, 170, 180
  See application file for complete search history.

(56) References Cited

U.S. PATENT DOCUMENTS

| 4,842,451 | A | * | 6/1989 | Dugger | 408/21 |
| 5,190,548 | A | * | 3/1993 | Davis | 606/80 |
| 5,895,179 | A | * | 4/1999 | Gschwend et al. | 408/226 |
| 7,041,107 | B2 | * | 5/2006 | Pohjonen et al. | 606/84 |
| 2004/0208717 | A1 | * | 10/2004 | Greenhalgh | 408/224 |
| 2011/0208194 | A1 | * | 8/2011 | Steiner et al. | 606/80 |

* cited by examiner

*Primary Examiner* — Nicholas Woodall
*Assistant Examiner* — Larry E Waggle, Jr.
(74) *Attorney, Agent, or Firm* — H. Jay Spiegel

(57) ABSTRACT

A drill bit has a cylindrical proximal end coupled to a driving device with a central axis of rotation about which the proximal end rotates. A distal portion of the drill bit is a cutting device attached to the proximal end in such a way that it extends outside the periphery of the proximal end for a distance less than the entirety of the circumference of the proximal end. A guide wire extends through a passageway in the bit and is provided to create a pilot hole before the distal portion enlarges that hole. With this configuration of the cutting device, it is possible to position the cutting device in the distal portion in a direction facing away from the medial femoral condyle so that the proximal end of the drill bit can slide past the medial femoral condyle, with its axis of rotation much closer to that condyle than would be the case in prior art drill bits.

11 Claims, 5 Drawing Sheets

CANNULATED DRILL BIT WITH RADIALLY OFFSET CUTTING EDGE

BACKGROUND OF THE INVENTION

The present invention relates to a cannulated drill bit with radially offset cutting edge. In the performance of orthopedic surgery such as, for example, a surgery known as double bundle ACL reconstruction, one procedure required to be performed is that of drilling a graft tunnel hole for the posterior lateral graft bundle in the lateral condyle of the femur. In order to perform this drilling procedure to the greatest advantage, it is best to place the tunnel sufficiently posterior to provide a proper location for the graft.

In so drilling the tunnel, it has been found that it is most advantageous to pass the drill bit as close as possible to the medial femoral condyle so that the hole is drilled in the most proper location.

Currently, drill bits that are employed have an axis of rotation that is the same for both the proximal and distal ends thereof. The proximal end of the drill bit is coupled to a drill that facilitates rotation of the proximal end about its axis of rotation. The distal portion of the drill bit has cutting surfaces that permit creation of the tunnel. The prior art drill bit is cannulated and is guided by a guide wire that may first cut a pilot hole for the graft tunnel hole, then guide the bit in enlarging the pilot hole. With known drill bits, the periphery of the distal portion, which extends about the circumference of the drill bit (FIG. 1), limits the ability to pass the drill bit close enough to the medial femoral condyle to optimize the location where the tunnel hole is created.

In the prior art, the usual technique employed involves passing a guidewire past the medial femoral condyle and into the posterior distal portion of the lateral notch to form the pilot hole. When this technique is employed, it is advantageous to place the guidewire deliberately close to the medial femoral condyle, however, using prior art drill bits, the closest the guidewire may be placed is limited to the drill bit radius plus the appropriate clearance between the periphery of the drill bit and the medial femoral condyle. For example, if a 10 mm drill bit is used (FIG. 1), this clearance is typically 1-2 mm, making the distance of the axis of rotation of the drill from the medial femoral condyle in the range of 5.5 to 6.5 mm. With such a close clearance, it is quite possible, if not probable, that the medial femoral condyle will interfere with proper placement of the periphery of the drill bit. In order to prevent damage to the medial condyle, sometimes, surgeons utilize a thin walled metal or other rigid "protector" used to shield the medial femoral condyle from the periphery of the drill bit. Of course, the shield has a finite thickness that may require increased spacing between the drill bit and the medial femoral condyle. Additionally, use of the "protector" introduces an additional aspect of complication to the procedure, which surgeons prefer to avoid.

As such, it would be advantageous if a system and procedure could be devised that would allow closer spacing between the drill bit and the medial femoral condyle so that the graft tunnel hole for the posterior lateral graft bundle could be placed in closer proximity to the deepest portion of the distal femoral notch.

It is with these thoughts in mind that the present invention was developed.

U.S. Published Patent Application No. US 2004/0220577 A1 to Cragg et al. discloses methods and apparatus for forming shaped axial bores through spinal vertebrae. Cragg et al. teach, in FIGS. 23 and 24 thereof, a drive shaft 236 to which is affixed a spherical drill bit 220 which is slightly offset from the axis of the drive shaft 236. However, as particularly shown in the figures, the ball 220 extends outside the entire periphery of the drive shaft and, as such, could not possibly achieve the goals and advantages of the present invention.

SUMMARY OF THE INVENTION

The present invention relates to a cannulated drill bit with radially offset cutting edge. The present invention includes the following interrelated objects, aspects and features:

(1) In a first aspect, the present invention contemplates a drill bit having a proximal end intended to be coupled to a driving device such as a drill that will impart rotation to the proximal end of the drill bit. The proximal end of the drill bit has a cylindrical shape and a central axis of rotation about which the proximal end rotates under the force imparted to it by the driving device.

(2) A distal portion of the drill bit comprises a cutting device. The cutting device is attached to the proximal end in such a way that it extends outside the periphery of the proximal end for a portion of the circumference of the proximal end. The bit is cannulated, allowing passage therethrough of a guide wire with a distal cutting surface allowing the guide wire to first create a pilot hole before guiding the distal portion in enlarging that hole to create the graft tunnel hole.

(3) With the configuration of the cutting device as described in paragraph (2) above, it is possible to position the cutting device in the distal portion of the drill bit in a direction facing away from the medial femoral condyle so that the proximal end of the drill bit can slide past the medial femoral condyle, with its axis of rotation much closer to that condyle than would be the case in prior art drill bits.

(4) In prior art devices, the distance from the medial femoral condyle to the axis of rotation of the drill bit varies as a function of drill bit diameter. In the present invention, as disclosed herein, this distance is fixed regardless of the diameter of the distal portion of the drill bit because the cutting surface of the distal portion does not extend entirely around the circumference of the bit.

(5) In this way, the cutting device may engage the distal femur at a location much closer to the center of the femoral notch by a matter of several millimeters than is the case with prior art devices. In this way, the graft tunnel may be created for the posterior lateral graft bundle at a more advantageous location than is possible in accordance with the teachings of the prior art.

Accordingly, it is a first object of the present invention to provide a cannulated drill bit with radially offset cutting edge.

It is a further object of the present invention to provide such a drill bit in which the cutting device on the distal portion thereof extends outside the periphery of the proximal end for a portion of the circumference of the proximal end.

It is a yet further object of the present invention to provide such a drill bit in which the proximal end may pass closer to the medial femoral condyle when being positioned for drilling a graft tunnel hole for the posterior lateral graft bundle in double bundle ACL reconstruction surgery than is the case with prior art drill bits.

It is a still further object of the present invention to provide such a drill bit in which a hole larger in diameter than the diameter of the proximal end thereof may be formed as a result of the structural features thereof.

These and other objects, aspects and features of the present invention will be better understood from the following detailed description of the preferred embodiment when read in conjunction with the appended drawing figures.

SPECIFIC DESCRIPTION OF THE PREFERRED EMBODIMENT

Figure 1:
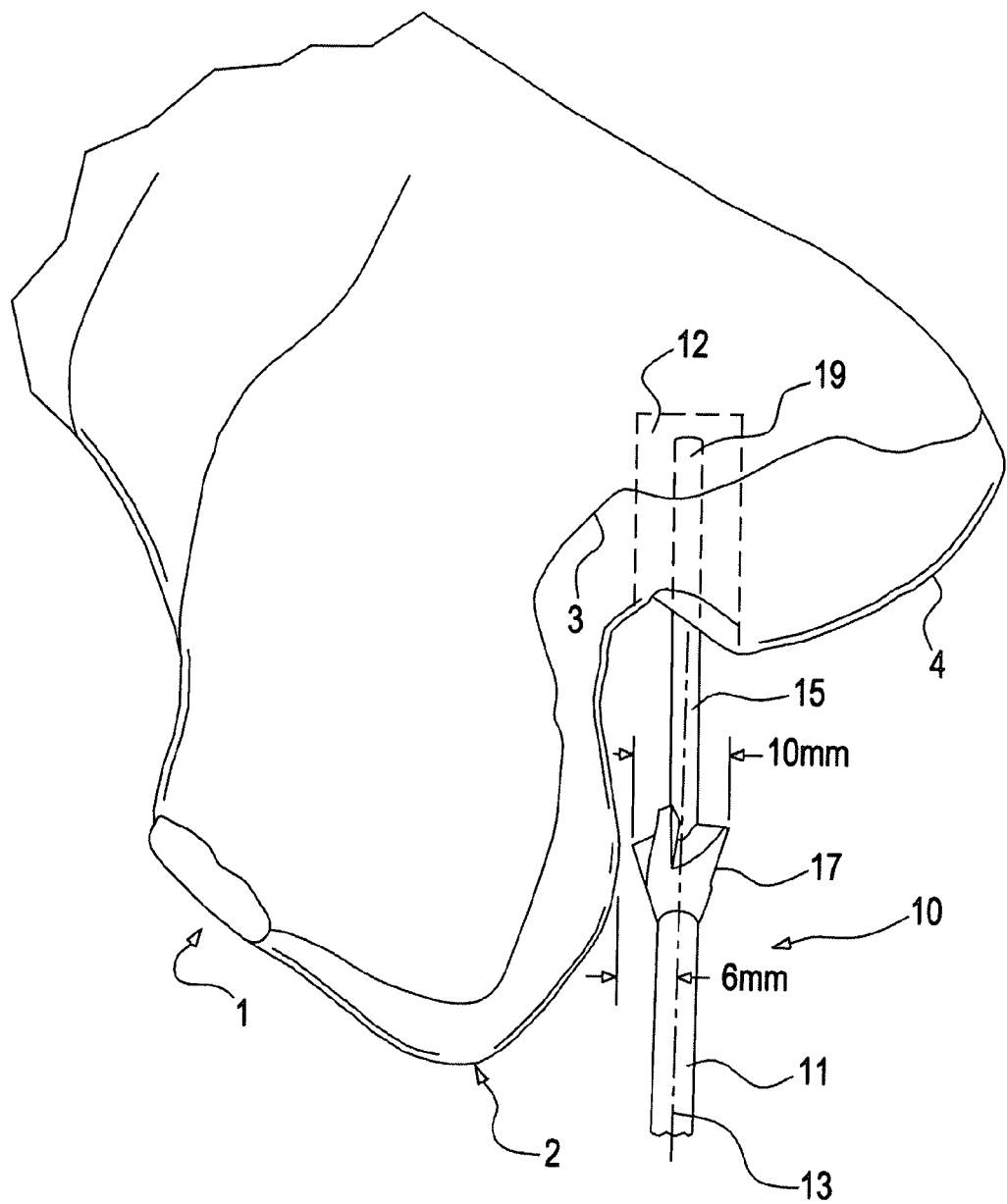
FIG. 1 shows a prior art drill bit being used to drill a graft tunnel hole in a distal femur.

Reference is first made to FIG. 1 which shows a distal femur 1 having a medial femoral condyle 2, an intercondylar notch 3, and a lateral femoral condyle 4.

With further reference to FIG. 1, a prior art drill bit 10 includes a proximal end 11 having an axis of rotation 13, a distal cutting member 17, and a guide wire 15 extending through an axial passageway formed through the bit 10. The cutting member 17 extends completely about the periphery of the bit 10. As seen in FIG. 1, the diameter of the cutting member 17 may be, for example, 10 mm and, for this size drill bit, the cutting member 17 passes about 1 mm from the medial femoral condyle when preparing to drill a graft tunnel hole 12 shown in phantom. The guide wire 15 has a distal cutting surface (not shown) that permits cutting a pilot hole 19 shown in phantom in FIG. 1, whereupon the distal cutting member 17, guided by the guide wire 15, enlarges the pilot hole 19 to form the graft tunnel hole 12. As explained above, it would be advantageous if the opening of the graft tunnel 12 could be located leftward in the view of FIG. 1 closer to the center of the intercondylar notch 3. The present invention addresses this problem.

Figure 2:
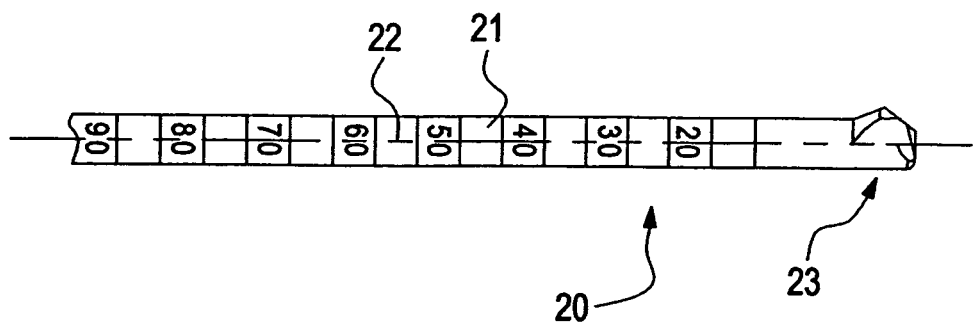
FIG. 2 shows a side view of the present invention.
Figure 3:
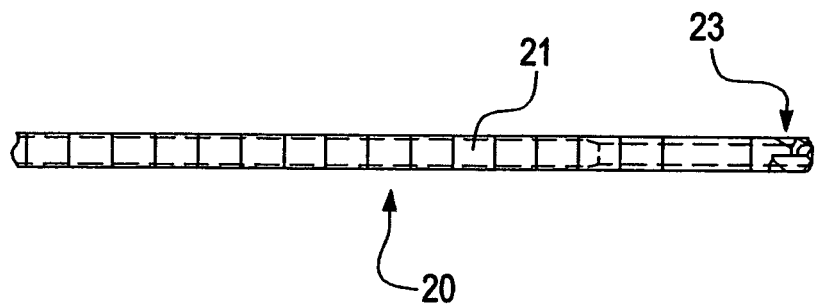
FIG. 3 shows a view similar to that of FIG. 2, but with the drill bit rotated 90° with respect to the view of FIG. 2.
Figure 4:
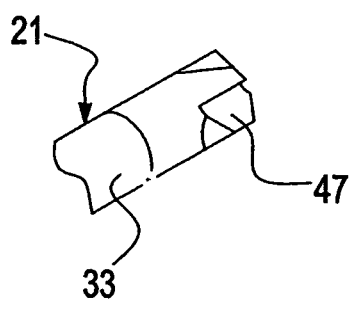
FIG. 4 shows a perspective view from the perspective of the line B-B of FIG. 2.
Figure 5:
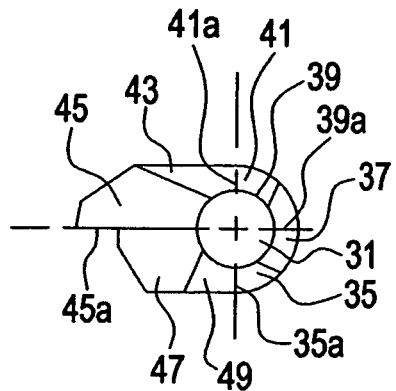
FIG. 5 shows a bottom view of the drill bit, looking from the distal end toward the proximal end thereof.
Figure 6:
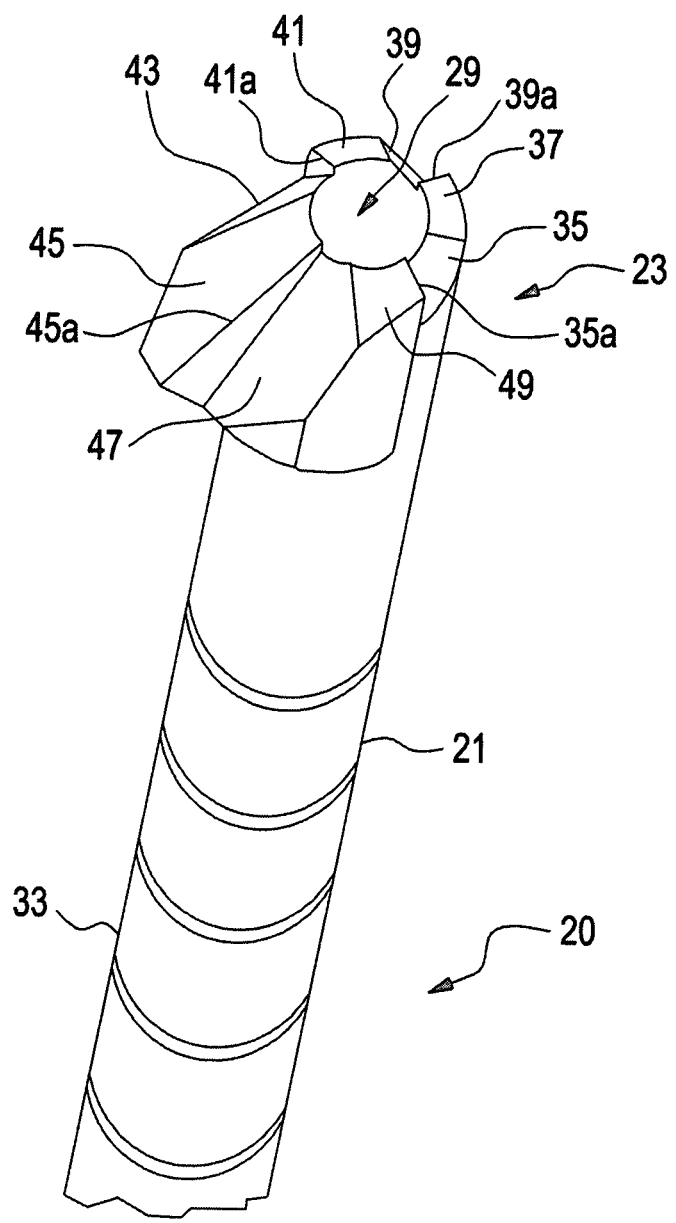
FIG. 6 shows a further perspective view of the inventive drill bit.
Figure 7:
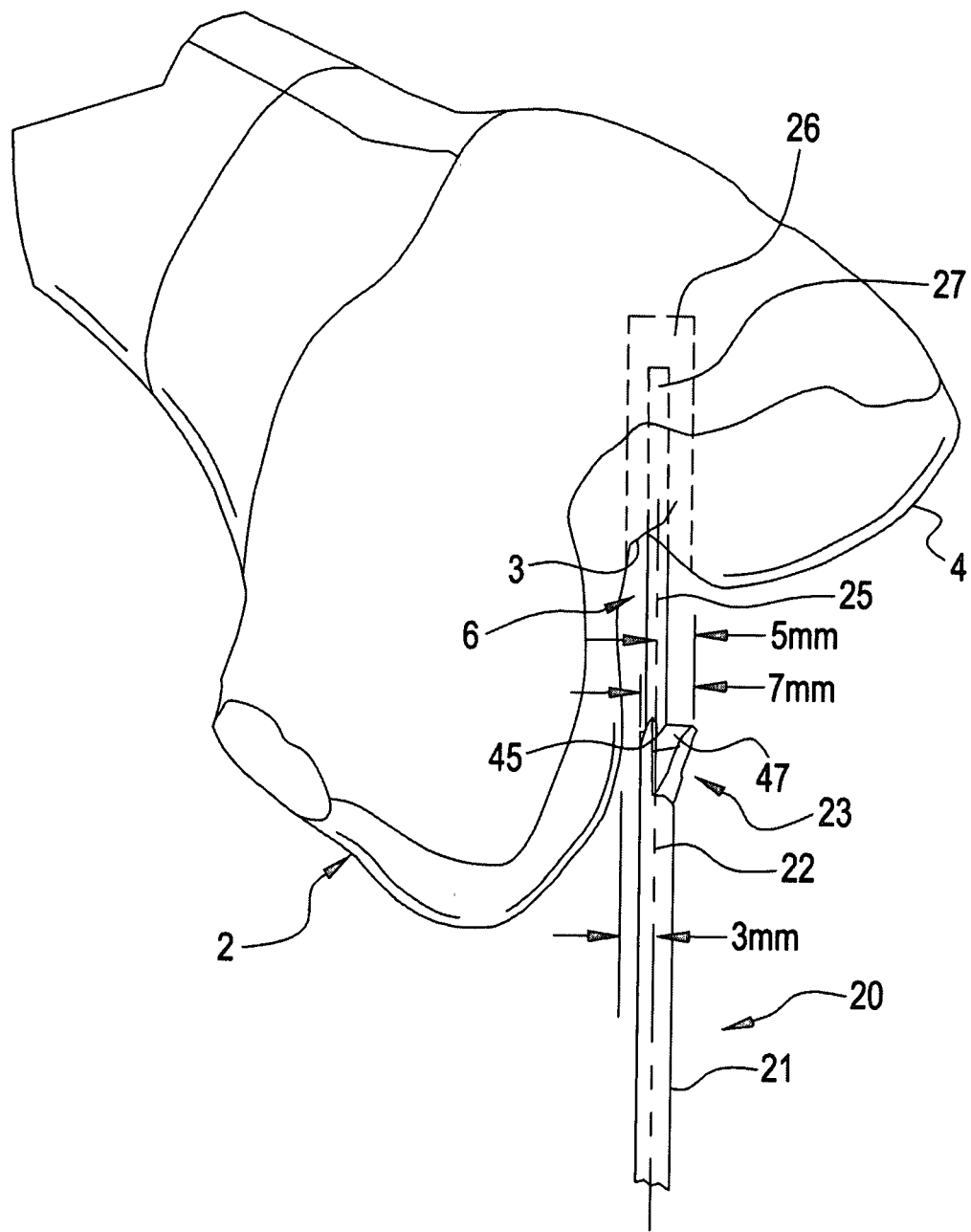
FIG. 7 shows a view similar to that of FIG. 1, but with the inventive drill bit shown able to drill a graft tunnel hole closer to the center of the intercondylar notch.

Reference is now made to FIGS. 2-6. FIGS. 2 and 3 show the inventive drill bit 20 in differing rotative positions thereof. As seen in the figures, the inventive drill bit has a proximal end 21 and a distal cutting portion 23. With reference to FIGS. 6 and 7, a guide wire 25 (FIG. 7) extends through the bore 29 (FIG. 6) aligned with the axis of rotation 22 of the proximal end 21 and has a distal cutting surface (not shown) designed to cut a pilot hole 27 (FIG. 7 in phantom) in the intercondylar notch, whereupon the distal cutting portion 23 guided by the guide wire 25 enlarges the pilot hole to create the graft tunnel hole 26 (in phantom) for a posterior lateral graft bundle, which hole extends into the lateral femoral condyle. As shown in FIG. 7, the guide wire 25 is generally cylindrical and smaller in diameter than the proximal end 21 since it must be slidably received in the bore 29. The guide wire 25 is omitted from FIGS. 2-6 for ease of understanding and viewing the rest of the structure of the inventive drill bit 20.

As shown in FIG. 2, the proximal end 21 has the central axis 22 about which the proximal portion rotates when it is coupled to a driving member such as a drill (not shown). The proximal end 21 is cylindrical in construction and includes the bore 29 extending therethrough. The bore 29 has an opening 31 at its distal end (FIG. 5) that facilitates extension therethrough of the guide wire 25.

With reference to FIG. 4, the cylindrical periphery 33 is seen. The distal cutting portion 23 (FIG. 5) includes a first circumferential region subtending approximately 180°, with a plurality of flutes or relief areas 35, 37, 39 and 41, and cutting edges 35a, 39a and 41a that surround the bore 29, but have radially outer terminations merging with the outer periphery 33 of the proximal end 21. In other words, these cutting edges face distally but do not extend radially outwardly beyond the surface of the periphery 33 of the proximal end 21.

However, with further reference to FIGS. 5-6, additional flutes or relief areas 43, 45, 47 and 49 and cutting edge 45a are provided in a second circumferential region also subtending 180°, which flutes or relief areas extend radially outwardly beyond the surface of the periphery 33 of the proximal end 21. With particular reference to FIGS. 5-6, the flutes 43, 45, 47 and 49 in combination subtend less than the entirety of the circumference of the proximal end 21. It will be understood that the circumferential extent of the first and second regions may vary, provided only that the first region merge with the periphery over a certain arcuate extent sufficient to pass by the medial condyle. In this way, as will be understood in greater detail hereinafter, the flutes 43, 45, 47 and 49 may be oriented through rotation of the proximal end 21 in a position facing away from the medial femoral condyle when the inventive drill bit 20 is being positioned in an advantageous location to begin drilling the graft tunnel 26. This positioning permits the drill bit 20 to pass closer to the medial femoral condyle than is the case in prior art drill bits such as, for example, the drill bit 10 depicted in FIG. 1.

FIG. 6 shows an enlarged perspective view of the proximal and distal portions of the drill bit 20 depicted by the reference numerals 21 and 23, respectively, including depiction of the bore 29 and the flutes 35, 37, 39, 41, 43, 45, 47 and 49, and cutting edges 35a, 39a, 41a and 45a.

Figure 8:
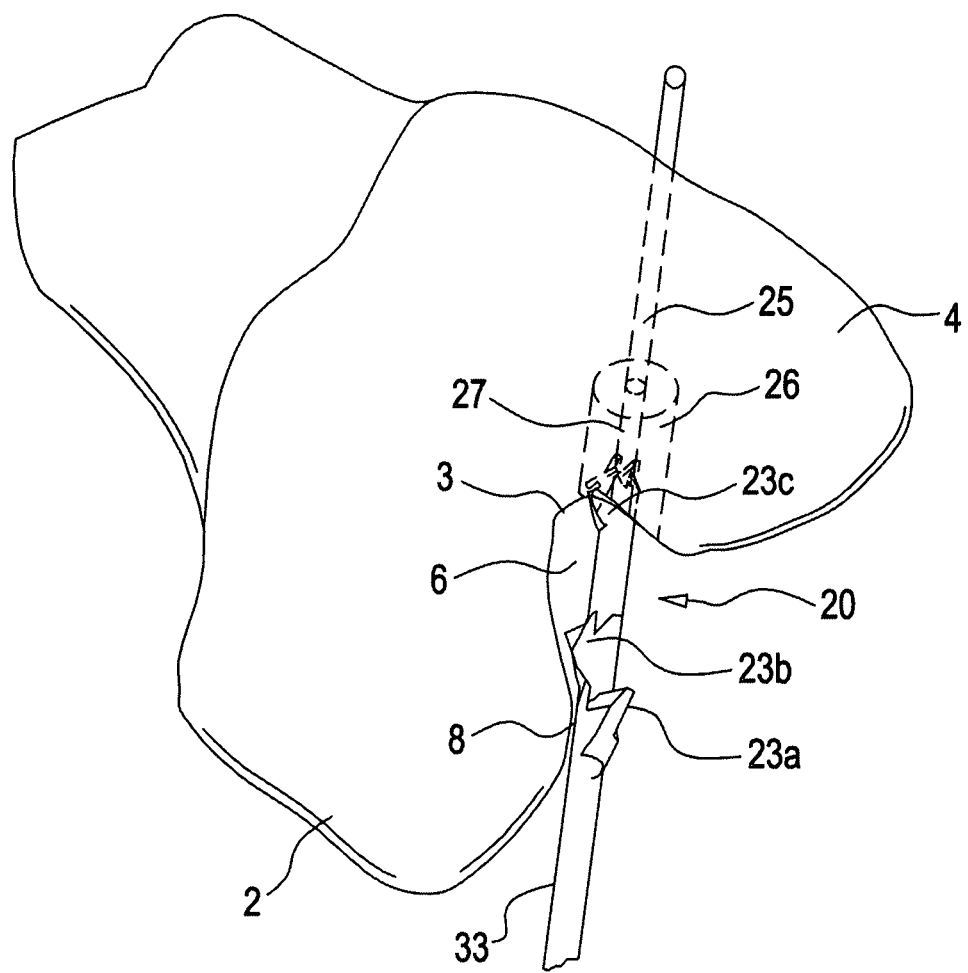
FIG. 8 shows a perspective view similar to that of FIG. 7, but showing the sequence of insertion of the inventive drill bit and drilling of the graft tunnel hole.

With reference to FIGS. 7-8, with the above description in mind, the advantages of the present invention over the prior art are readily evident. As a first matter, whereas the distal portion 17 of the prior art drill bit 10 (FIG. 1) has a uniform diameter of 10 mm, the lateral-most dimension of the largest flute or relief area 47 of the distal portion 23 of the inventive drill bit 20 by contrast has a diameter of 7 mm and extends from the axis of rotation 22 a maximum extent of 5 mm radially beyond periphery 33, with that extent being no more than 2 mm in the other direction. In this way, the distal cutting portion 23 of the drill bit 20 may be situated laterally closer to the medial femoral condyle 2 than is the case with the drill bit 10, thereby enabling the creation of a 10 mm graft tunnel situated more medially while still maintaining a 1 mm spacing between periphery 33 and the medial condyle. In fact, the distance between the axis of rotation 13 and the medial condyle, in the case of the prior art drill bit 10, is 6 mm while the distance between the axis of rotation 22 and the medial condyle, in the case of the drill bit 20, is 3 mm. This 3 mm improvement is crucial in facilitating locating the graft tunnel hole 26 opening much closer to the center of the intercondylar notch 3 in the case of the drill bit 20 than is possible when the drill bit 10 is used to drill the tunnel 19 as shown in FIG. 1.

As known to those of ordinary skill in the art, the difference of 3 mm resulting from practicing the teachings of the present invention is crucial in properly anatomically locating the location of the graft tunnel hole 26 for the purpose of receiving a posterior lateral graft bundle in the performance of double bundle ACL reconstruction surgery.

Once the distal cutting portion 23 has, without rotation, passed by the closest portion of the medial femoral condyle 2, it enters a wider area designated by the reference numeral 6, where it may rotate including with the cutting edge 45*a* facing the medial lateral condyle 2 without engaging that condyle, so that the tunnel 26 may safely be drilled without any damage being caused to the medial femoral condyle 2.

FIG. 8 shows a variety of rotative and longitudinal positions of the cutting portion 23, such positions encountered in the course of using drill bit 20. In the orientation designated by the reference numeral 23*a*, the cutting portion 23 is rotated to a position facing away from the medial femoral condyle 2 so that it may be slipped by the closest portion of the medial femoral condyle as guided by the previously placed guide wire 25. Once it has slipped past that structure of the medial femoral condyle, it enters the wider area 6 where it is designated 23*b* and is free to rotate as driven by a driving device (not shown) to begin the drilling process when cutting portion 23 is in position 23*b*. The closest edge of the medial femoral condyle is shown by the line designated by the reference numeral 8 in FIG. 8, and it is spaced approximately 1 mm from periphery 33. Reference numeral 23*c* shows the cutting portion 23 drilling the graft tunnel hole 26 by enlarging the pilot hole 27 formed by the guide wire 25.

FIGS. 7-8 clearly show the advantages of the present invention over the prior art since they demonstrate how the inventive drill bit 20 may be twisted to an orientation permitting it to be slipped past the medial femoral condyle 2 to a location where it may be activated to drill the graft tunnel hole 26 in a location closer to the intercondylar notch 3 than is possible with any prior art drill bit.

While the present invention has been described in terms of an example in which it may advantageously be used to create a graft tunnel in the performance of double bundle ACL reconstruction surgery, it also may be advantageously employed in any surgical situation where a similar problem exists, that of permitting a drill bit to pass by bony structure closer than is possible through the use of prior art drill bits.

The inventive drill bit 20 may be made of any desired materials typically used in the manufacture of drill bits employed in the performance of orthopedic surgery.

Accordingly, an invention has been disclosed in terms of a preferred embodiment thereof which fulfills each and every one of the objects of the invention as set forth hereinabove, and provides a new and useful cannulated drill bit with radially offset cutting edge of great novelty and utility.

Of course, various changes, modifications and alterations in the teachings of the present invention may be contemplated by those of ordinary skill in the art without departing from the intended spirit and scope thereof. Such variations include the use of a greater or lesser number of cutting edges and different diameters and dimensions than those used to describe the preferred embodiment disclosed above.

As such, it is intended that the present invention only be limited by the terms of the appended claims.

The invention claimed is:

1. A drill bit for performance of orthopedic surgery and having a circumference, comprising:
   a) a proximal end adapted to be coupled to means for rotating said bit, said proximal end having an axis of rotation and a periphery;
   b) said proximal end having a distal termination to which is attached a distal cutting portion, said distal cutting portion including a first circumferential region extending partially about said circumference and having a plurality of distally facing cutting edges comprising flutes and a second circumferential region with at least one cutting edge located between two of said flutes and extending partially about said circumference, there being no circumferential overlap between said first and second regions;
   c) said cutting edges in said first region not extending radially beyond the periphery of said proximal end;
   d) at least one of said at least one cutting edge in said second region extending radially outwardly beyond said periphery;
   e) said second region extending less than an entirety of the circumference of said bit.

2. The bit of claim 1, wherein said second region comprises a plurality of cutting edges.

3. The bit of claim 2, wherein said plurality of cutting edges of said second region comprise a first cutting edge and a second cutting edge.

4. The bit of claim 3, wherein said first cutting edge extends radially outwardly further than said second cutting edge.

5. The bit of claim 1, further including a passageway therethrough sized to receive a guide wire, said passageway being aligned with said axis of rotation.

6. The bit of claim 5, wherein said guide wire is smaller in diameter than said proximal end.

7. The bit of claim 1, wherein said proximal end is tubular.

8. A tubular drill bit for performance of orthopedic surgery and having a circumference, comprising:
   a) a proximal end adapted to be coupled to means for rotating said bit, said proximal end having an axis of rotation and a periphery;
   b) said proximal end having a distal termination to which is attached a distal cutting portion, said distal cutting portion including a first circumferential region extending partially about said circumference and having a plurality of distally facing cutting edges comprising flutes and a second circumferential region with at least one cutting edge located between two of said flutes and extending partially about said circumference, there being no circumferential overlap between said first and second regions;
   c) said cutting edges in said first region not extending beyond the periphery of said proximal end;
   d) at least one of said at least one cutting edge in said second region extending radially outwardly beyond said periphery;
   e) said second region extending less than an entirety of a circumference of said bit; and
   f) a passageway aligned with said axis of rotation and sized to receive a guide wire therethrough.

9. The bit of claim 8, wherein said second region includes a plurality of cutting edges comprising at least a first cutting edge and a second cutting edge.

10. The bit of claim 9, wherein said first cutting edge of said second region extends radially outwardly further than said second cutting edge thereof.

11. The bit of claim 8, wherein said guide wire is smaller in diameter than said proximal end.

\* \* \* \* \*